US011159532B2

(12) United States Patent
Barnes et al.

(10) Patent No.: US 11,159,532 B2
(45) Date of Patent: *Oct. 26, 2021

(54) SYSTEMS AND METHODS FOR USE IN MANAGING ACCESS TO USER PROFILES, AND CONTENT BLOCKS INCLUDED THEREIN

(71) Applicant: MASTERCARD INTERNATIONAL INCORPORATED, Purchase, NY (US)

(72) Inventors: Andrew Christopher Barnes, St. Peters, MO (US); Eric Orlaska, O'Fallon, MO (US); Mary Thuet, Ballwin, MO (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 135 days.

This patent is subject to a terminal disclaimer.

(21) Appl. No.: 16/667,468

(22) Filed: Oct. 29, 2019

(65) Prior Publication Data

US 2020/0067925 A1 Feb. 27, 2020

Related U.S. Application Data

(63) Continuation of application No. 15/399,276, filed on Jan. 5, 2017, now Pat. No. 10,476,876.

(51) Int. Cl.
*H04L 29/06* (2006.01)
*G16H 10/60* (2018.01)
*G06F 21/62* (2013.01)

(52) U.S. Cl.
CPC .......... *H04L 63/10* (2013.01); *G06F 21/6245* (2013.01); *G16H 10/60* (2018.01); *G06F 2221/2137* (2013.01)

(58) Field of Classification Search
CPC ..... H04L 63/10; G16H 10/60; G06F 21/6245; G06F 2221/2137
See application file for complete search history.

(56) References Cited

U.S. PATENT DOCUMENTS 8,019,620 B2 9/2011 Miller et al.
10,476,876 B2 11/2019 Barnes et al.
(Continued)

FOREIGN PATENT DOCUMENTS

WO WO2004/102393 11/2004

*Primary Examiner* — Samson B Lemma
*Assistant Examiner* — Zoha Piyadehghibi Tafaghodi
(74) *Attorney, Agent, or Firm* — Harness, Dickey & Pierce, P.L.C.

(57) ABSTRACT

Systems and methods are provided for use in implementing access controls to content blocks of a user profile associated with a user. One exemplary system includes an access engine configured to receive an access command from a user, via a communication device, to access the user profile. The access command includes a designation of at least one the content blocks for access by a provider, an identity of the provider, and a duration of the access. The access engine is configured to also modify a permission associated with the designated content block(s) in relation to the provider to permit the access by the provider, and to expose the content block(s) to the provider, thereby granting the access for the provider to the content block(s). The access engine is configured to further terminate the access of the provider to the content block(s) when the duration of the access expires.

19 Claims, 3 Drawing Sheets

(56) References Cited

U.S. PATENT DOCUMENTS

| | | | |
|---|---|---|---|
| 2006/0229918 A1* | 10/2006 | Fotsch | G16H 10/60 705/3 |
| 2008/0172737 A1* | 7/2008 | Shen | G06F 21/6245 726/21 |
| 2012/0239417 A1* | 9/2012 | Pourfallah | G06Q 20/384 705/2 |
| 2013/0204886 A1 | 8/2013 | Faith et al. | |
| 2014/0033324 A1* | 1/2014 | Kiang | H04L 67/2861 726/27 |
| 2015/0207699 A1 | 7/2015 | Fargano et al. | |
| 2016/0328577 A1* | 11/2016 | Howley | G06F 1/3215 |
| 2016/0337369 A1* | 11/2016 | Sanso | H04L 63/102 |
| 2016/0337377 A1* | 11/2016 | Grube | G06F 3/064 |
| 2018/0191722 A1 | 7/2018 | Barnes et al. | |

\* cited by examiner

SYSTEMS AND METHODS FOR USE IN MANAGING ACCESS TO USER PROFILES, AND CONTENT BLOCKS INCLUDED THEREIN

CROSS-REFERENCE TO RELATED APPLICATION

This application is a continuation of U.S. patent application Ser. No. 15/399,276 filed on Jan. 5, 2017. The entire disclosure of the above application is incorporated herein by reference.

FIELD

The present disclosure generally relates to systems and methods for use in managing access to and exchange of user profiles, and in particular, to managing access to content blocks included in the user profiles (and potential exchange thereof and/or data relating thereto).

BACKGROUND

This section provides background information related to the present disclosure which is not necessarily prior art.

People often disseminate information about themselves to providers in connection with various activities. For example, when a person (e.g., as a patient, etc.) visits a doctor's office (broadly, a provider), the person is typically invited to share contact information with the office, along with appropriate health information. Likewise, when the person (e.g., as a consumer, etc.) orders a product from a merchant (broadly, a provider), the merchant may collect certain information from the person to help ensure the product is properly delivered to the person and to allow the merchant to respond to any inquiries from the person. In both cases, at least some of the information gathered from the person by the providers may be the same (e.g., contact information, etc.).

Separately, it is known for providers to store information collected from people (e.g., patients, consumers, etc.) for subsequent use in addressing the people's needs and/or to facilitate additional contact with the people (e.g., reminders of annual check-ups, offers for additional products, etc.). In so doing, the information is generally stored in secure locations, and may further be shared with different partners of the providers for various purposes (e.g., upon appropriate disclosure to the people whose information is being shared, upon receiving appropriate permissions from such people, etc.).

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
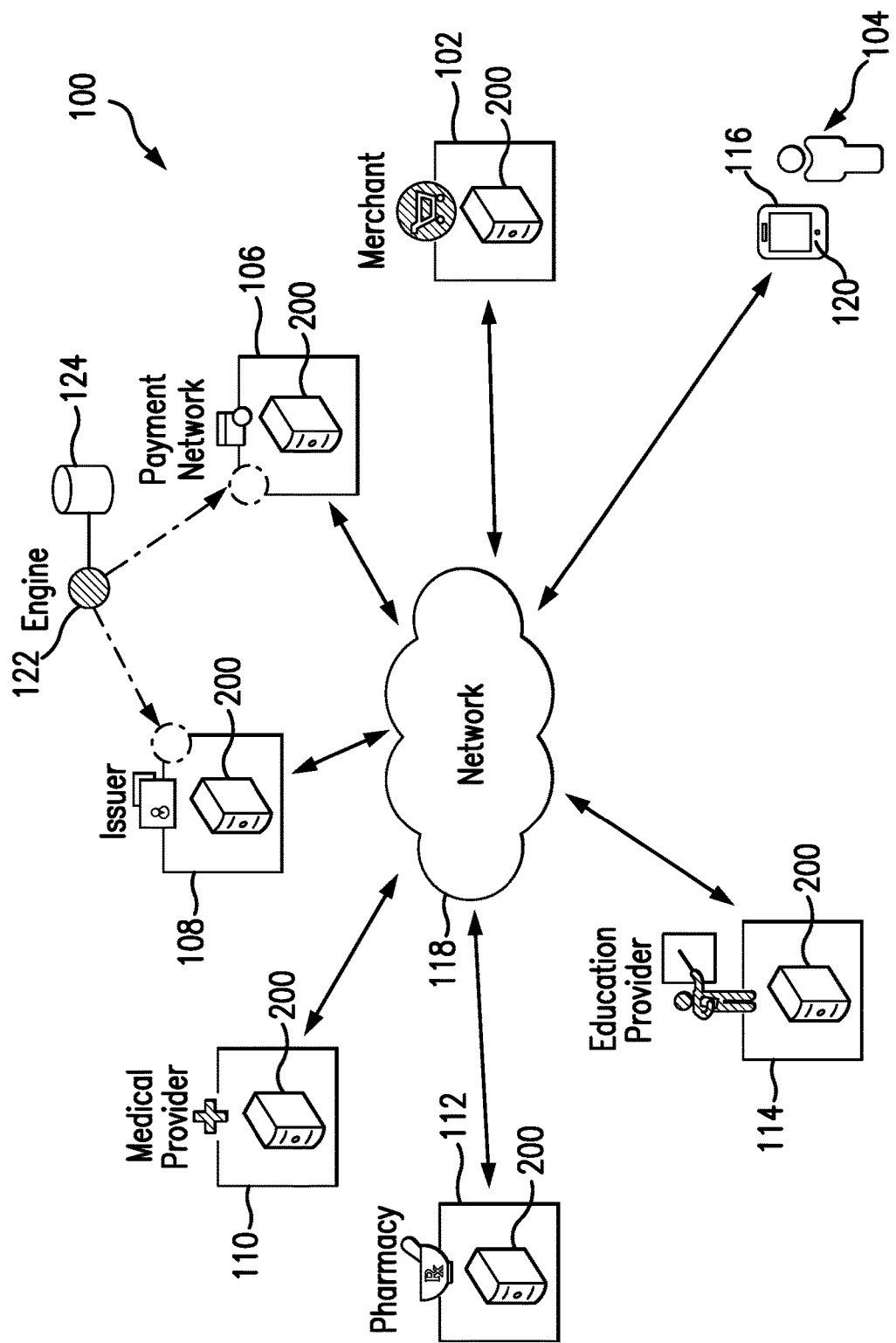
FIG. 1 is a block diagram of an exemplary system of the present disclosure suitable for use in managing access to a user profile associated with a user, by providers engaged by the users for one or more services.

The description and specific examples included herein are intended for purposes of illustration only and are not intended to limit the scope of the present disclosure.

People (broadly, users herein) often interact with providers to purchase products in the form of both services and goods. For certain products, the people are often invited, or required, to provide information to the providers associated with the products. The information may be personal and confidential to the people, and/or may include information repeatedly requested from multiple different providers.

Uniquely, the systems and methods herein permit users to compile profiles, which contain multiple content blocks of different information related to the users, and to provide access to the profiles (and/or the content blocks therein) to select providers so that the providers can retrieve desired or required information about the users (and/or other people associated with the users). In particular, in developing a profile for a user, an access engine interacts with a profile application at a communication device associated with the user. The access engine permits the user to compile different content blocks into the profile, where each of the content blocks may include different content relating to the user, for example, contact information, payment account credentials, medical history, allergies, forms, etc. Once the profile is compiled, the access engine further interacts with the profile application to permit the user to grant access to particular content blocks within the created profile (and the information therein) to certain providers for a particular duration. In so doing, the user may initiate the access (and identify the particular content blocks for such access) for the providers, or a provider may specifically request the access whereupon the access engine solicits the permission from the user via the profile application. Thus, through the systems and methods herein, the user is provided with a repository of information in his/her profile, which may be "opened" at the discretion (and permission) of the user for select providers to access (without a need to separately and repeatedly provide the same information to different providers). This allows a more efficient dissemination of the user's information to providers and facilitates enhanced security for the information.

As an example, a user may compile a content block in their profile at a computing device associated with their business card (e.g., containing information such as contact information, business position, company logo, etc.). In turn, when the user interacts with a provider (broadly, a recipient) and wants to provide their business card information to the provider in connection with such interaction, the user can simply grant access to their business card data block by the provider to exchange business cards (e.g., transmit their business card to the provider and/or receive the provider's business card, if applicable, via a network connection, etc.).

Additional exemplary embodiments will now be described more fully with reference to the accompanying drawings.

FIG. 1 illustrates an exemplary system 100, in which the one or more aspects of the present disclosure may be implemented. Although the system 100 is presented in one arrangement, other embodiments may include the parts of the system 100 (or other parts) arranged otherwise depending on, for example, the number and/or type of providers included, etc.

Generally, the system includes a merchant 102 that offers for sale, and sells, products (e.g., goods and services, etc.) to consumers, including, for example, to user 104 (e.g., as a consumer, etc.). The merchant 102 may include any type of merchant offering any types of products for sale to the consumers through purchase transactions, which may be funded by cash, check, payment accounts, etc. In addition, the merchant 102 may include different locations for offering the products for sale, and for selling the products to the consumers, including one or more brick-and-mortar locations and/or one or more virtual locations (e.g., websites, etc.), etc.

In connection with a payment account transaction between the merchant 102 and the user 104 for the purchase of a product, the user 104 provides certain information to the merchant 102 relating to a payment account to be used in the transaction. Such information may include, for example, payment account credentials, and/or other information to authenticate the user 104, etc. In response, the merchant 102 interacts with a payment network 106 and an issuer 108 of the user's payment account (e.g., via an acquirer (not shown) associated with the merchant 102, etc.), each included in the system 100, to authorize the transaction. In addition, apart from the payment account transaction (and the information related thereto), the merchant 102 may also request additional information from the user 104 such as, for example, contact information, etc., to facilitate delivery of the product, to assign warranty features for the product, and/or to implement other services related to the product. Often, such additional information (and its content) is based on the type of the product being purchased by the user 104 from the merchant 102. For example, a purchase of lawn services may require different such additional information from the user 104 (apart from payment account information), as compared to a purchase of a television or a vehicle.

Separately, in connection with the payment account issued to the user 104 by the issuer 108, the issuer 108 may further offer additional banking products to the user 104. For example, the issuer 108 may offer products to the user 104 relating to loans, mortgages, checking accounts, etc. Like above, the user 104 is generally requested or required to provide certain information to the issuer 108 to enroll or otherwise take advantage of such additional banking products.

The illustrated system 100 also includes a medical provider 110 and a pharmacy 112. The medical provider 110 includes any type of institution or entity that offers medical services (in any form) to the user 104 or that makes such services available to the user 104, and/or any people associated with the user 104 (e.g., a son, a daughter, a parent, a spouse, etc.). For example, the medical provider 110 may include a doctor (and/or an office associated with the doctor), a clinic, a hospital, a medical imaging provider, a lab, etc. The pharmacy 112 may include any institution or entity that offers and/or delivers health and/or medical products to the user 104 (and/or to the people associated with the user 104), including specifically, for example, pharmaceuticals, etc. In connection with the medical provider 110 and/or the pharmacy 112, the user 104 generally provides information (e.g., medical history, allergy information, etc.) to the medical provider 110 and/or the pharmacy 112 regarding the user 104, and potentially the people associated with the user 104, to facilitate medical services and/or delivery of pharmaceuticals, for example.

Further, the system 100 includes an education provider 114. The education provider 114 may include any type of institution, or entity, which offers education services to the user 104, and/or to the people associated with the user 104. In one example, the education provider 114 may include an elementary school for the user's child. Regardless of type, like above, the user 104 is generally requested or required to provide information to the education provider 114 regarding the user 104 (and/or the people associated with the user 104) to facilitate and/or to qualify the user 104 for the education services from the education provider 114. For example, in connection with the above example where the education provider 114 may include the elementary school, the user 104 may be required to submit a permission slip for the user's child to attend a field trip or other event, while also providing allergy and/or vaccination records to medical personnel of the education provider 114 (e.g., a school nurse, etc.).

With that said, it should be appreciated that the merchant 102, the issuer 108, the medical provider 110, the pharmacy 112, and the education provider 114, as described above, may each be considered a provider herein. It should also be appreciated that while only one merchant 102, one user 104, one payment network 106, one issuer 108, one medical provider 110, one pharmacy 112, and one education provider 114 are illustrated in FIG. 1, a different number of each (e.g., potentially tens or hundreds, etc.) may be included in other system embodiments. In addition, it should be appreciated that the particular providers illustrated in FIG. 1 (the merchant 102, the issuer 108, the medical provider 110, the pharmacy 112, and the education provider 114) are included for purposes of illustration only, and do not limit the scope of the present disclosure, as numerous other providers may be included in the system 100 in other embodiments. In connection therewith, when various other providers are present, it should be appreciated that the user 104 may interact with such various other providers, whereupon information exchange between the user 104 and the various other providers is necessary, required, and/or desired.

With continued reference to FIG. 1, the merchant 102, the user 104 (via his/her communication device 116), the payment network 106, the issuer 108, the medical provider 110, the pharmacy 112, and the education provider 114 are each coupled to (and in communication with) network 118. The network 118 may include, without limitation, a local area network (LAN), a wide area network (WAN) (e.g., the Internet, etc.), a mobile network, a virtual network, a Bluetooth/personal area network, and/or another suitable public and/or private network capable of supporting communication among two or more of the parts illustrated in FIG. 1, or any combination thereof. For example, network 118 may include multiple different networks, such as a private payment transaction network made accessible by the payment network 106 to the merchant 102 and the issuer 108, and, separately, the public Internet, which may be accessible to the user 104 (via the communication device 116), the medical provider 110, the pharmacy 112, the education provider 114, and/or any other part of the system 100, etc. as desired.

The communication device 116 associated with the user 104 may generally be understood to be a portable communication device such as, for example, a mobile phone, a personal digital assistant (PDA), a tablet, a laptop, or other computing device suitable to be portable and/or carried by the consumer 104, etc. (although this is not required in all embodiments). As shown, the communication device 116 includes a profile application 120, which is configured (via executable instructions) to operate as described herein. In addition, in some embodiments, the profile application 120 may include, or form part of, a virtual wallet application, such as for example, MasterPass®, Apple Pay®, Samsung Pay®, PayPal®, Google Wallet®, Android Wallet™, etc., which configures the communication device 116 to act as a payment device, for and/or with one or more different payment accounts (e.g., the payment account issued to the user 104 by the issuer 108, etc.). Alternatively, in other embodiments, the profile application 120 may include a standalone application at the communication device 116. With that said, when the communication device 116 is described as configured to perform various operations herein, it should be appreciated that it may be doing so generally in coordination with the application 120 (even if the application 120 is not specifically referenced), or not.

The illustrated system 100 further includes an access engine 122, and a profile data structure 124 coupled to the access engine 122. The access engine 122 is configured by executable instructions to interact with the profile application 120 (at the user's communication device 116), as well as the merchant 102, the issuer 108, the medical provider 110, the pharmacy 112, and the education provider 114 (and any other providers potentially included in the system 100). In FIG. 1, the access engine 122 is illustrated as separate and apart from the payment network 106 and the issuer 108. However, as indicated by the dotted lines, the access engine 122 may be incorporated (in part or in whole) in one or more of the payment network 106 and the issuer 108 in other system embodiments. What's more, the profile data structure 124 may be incorporated into the access engine 122, or it may be separate therefrom. Generally, however, when the access engine 122 is incorporated into the payment network 106 and/or the issuer 108 (in part or in whole), the profile data structure 124 is likewise incorporated.

In general in the system 100, in connection with the payment account issued to the user 104 by the issuer 108, for example, or apart therefrom, the user 104 may download and install the profile application 120, and further register to the access engine 122 (potentially in connection with configuring the profile application 120, or separate therefrom). In so doing, as part of the registration, the access engine 122 is configured to cause multiple interfaces to be displayed at the communication device 116, via the profile application 120, to solicit information from the user 104 to be included in a user profile for the user 104 (i.e., the user 104 generates a new user profile or updates an existing user profile). The user 104 may respond with all solicited content, or a portion thereof, through the profile application 120. In response to the content from the user 104, the access engine 122 is configured to then compile the user profile and to store the user profile in the profile data structure 124 (as a centralized repository, etc.).

Specifically, for example, as part of the registration, the access engine 122 may be configured to initially provide a generic user profile (as a shell) to the user 104 (via the multiple interfaces). The generic user profile may be divided into multiple content blocks, each relating to different information about the user 104. Basically, the user profile is divided into the content blocks based on the premise that the user 104 will then be able to grant access to the information included in the profile on a block-by-block basis. As such, in this example, contact information will often be included in a different block than medical history. With that in mind, the resulting user profile for the user 104 may include a different content block relating to a plurality of different information, such as, without limitation, contact information for the user 104, payment account credentials, medical history (e.g., prior surgeries, preexisting conditions, etc.), current medication for the user 104, allergies, demographic information, insurance information, behavioral information, purchase history, parental consent, calendar information, contact history, preferences, etc. And, while the various different content blocks may include different information regarding the user 104, each is based on a common standard (such that the content in the various different blocks is generally standardized) to allow both senders and receivers to understand the content, for example, without further processing, etc. (e.g., to allow senders and receivers to interpret information through a common format, etc.).

The division of the user profile into the different content blocks (and the number and/or type of such content blocks) may be defined by the access engine 122, the user 104, and/or another person associated therewith. For example, the user 104, via the profile application 120, may define specific content blocks to be included in the user profile at registration (or thereafter), and also provide information for including in the content blocks. In particular, the profile application 120 may be configured to define a content block based on various inputs from the user 104 (at the communication device 116), and to then provide the content block (and associated information) to the access engine 122. In turn, the access engine 122 is configured to store the content block in the user profile for the user 104, in the profile data structure 124. This may then be repeated for multiple additional content blocks, as desired by the user 104. In at least one embodiment, the profile application 120 may be configured to provide information relating to the user 104 (or others associated with the user 104), automatically or otherwise, based on data captured and/or generated by the communication device 116 (or by applications at the communication device 116) at various times (e.g., location data for the communication device 116, heart rate data for the user 104, blood pressure for the user 104, a step count for the user 104, caloric expenditures for the user, activity versus rest intervals, purchase information, etc.). Here, for example, the profile application 120 may be configured to submit location information to the access engine 122 to be stored as part of the user profile in a location content block of the user's profile, and heart rate information to be stored as part of a health history content block of the user profile.

In various embodiments, one or more of the providers in the system 100 (e.g., one or more of the merchant 102, the issuer 108, the medical provider 110, the pharmacy 112, and the education provider 114; etc.) may also (or alternatively) be configured to access and edit the user profile for the user 104 at the profile data structure 124 (e.g., in general or a particular content block thereof, etc.), by adding and/or removing content blocks, by adding or removing or otherwise editing information in the content blocks, etc., either directly with the access engine 122 and/or through the profile application 120. For example, the merchant 102 may be configured to alter the user profile for the user 104 based on a purchase by the user 104 at the merchant 102 (e.g., via the profile application 120 when included as part of a virtual wallet application used in the purchase transaction at the merchant 102, etc.), to update the user profile to reflect the purchase (e.g., to append a receipt for the product to an appropriate content block of the user profile, to append warranty information for the product to an appropriate content block of the user profile, etc.). As another example, the medical provider 110 may be configured to append a prescription and/or additional medical history to the user profile for the user 104, via interaction with the access engine 122.

Regardless of the source of the content blocks in the user profile for the user 104, or the source of the information included therein (e.g., be it the user 104, a person associated with the user 104, or one of the providers associated with the user 104, etc.), it should be appreciated that the user profile may change, or expand, or shrink, from time to time, as information about the user 104 (and/or the people associated with the user 104) changes. Moreover, associations with different providers with which the user 104 (and/or the people associated with the user 104) interact may require and/or suggest a need for additional or different information to be included in the user profile (and different content blocks). Thus, as described, the profile application 120 and the access engine 122 are configured to cooperate to permit the user profile to change, expand, or shrink, as access is granted by the user 104.

In the illustrated embodiment (and as indicated above), the information included in the user profile for the user 104, in the profile data structure 124, is generally restricted to a standard format. That is, the access engine 122 is configured to enforce a standard format for the user profile when compiling it and storing in in the profile data structure 124 (e.g., in connection with defining data fields in the profile, formats, semantics, etc. for domain-specific groupings of information that the user 104 may choose to store and transmit as part of the profile, etc.). In one exemplary embodiment, the standard format may be based on (but is not limited to) open standards such as, for example, JSON, XML, Name-Value Pairs, etc. to enable a wide variety of sending and receiving devices (e.g., computing devices, Internet of Things (IoT) devices, etc.) to interact with the user profile for the user 104. With that said, each unique type of content block in the user profile (e.g., medical information, contact information, etc.) may be described in a specification/schema to include semantic definitions of each field, data type, data length, and required/optional indicator included in the content block. Then, when the content block is transmitted between the user 104 and a provider, it contains a header to indicate the content block type, followed by the values of the fields described in the schema. The format of the content block is then based on the chosen standard above (e.g., JSON, XML, Name-Value Pair, etc.).

Also in the illustrated embodiment, the access engine 122 may be configured to provide encryption of the user profile (and the information included therein) as stored in the profile data structure 124 and as received into and/or transmitted from the profile data structure 124. As can be appreciated, such encryption helps ensure security of the information contained in the user profile for the user 104. Specially, for example, the information contained in the user profile may be encrypted both at rest (e.g., as stored in the data structure 124, etc.) and in motion (e.g., when transmitted, etc.). In so doing, the encryption provided by the access engine 122 may include, without limitation, current industry standards such as AES-256 or Triple DES, etc.

Apart from compiling and storing (and generally managing) the user profile for the user 104 in the system 100, the profile application 120 and the access engine 122 cooperate to provide access, as granted by the user 104, to the user profile to various ones of the providers associated with the user 104. Such access may be based on a request by a provider, as received by the profile application 120. Or, such access may be based on a request by a provider, as received by the access engine 122 (whereby the access engine 122 solicits such access from the user 104 on behalf of the provider, for example, via the profile application 120). In some cases, such access may also be based on a particular request by the user 104 to allow such access to a provider (or to multiple providers). In addition, the access may be granted by the user 104 based on the particular content block comprising the desired information, or the access may be based on a combination of the content block and the particular provider desiring such information. Further, the user 104 can grant specific access based on the particular content block and/or provider at issue, for example, read only access (indefinitely, or for a specific time period, or when the consumer's communication device 116 is in proximity to the given provider), write only access (indefinitely, or for a specific time period, or when the consumer's communication device 116 is in proximity to the given provider), and read/write access (indefinitely, or for a specific time period, or when the consumer's communication device 116 is in proximity to the given provider). Or, the user 104 can grant "default" access that would apply for any content block/provider combination not specified.

In particular, for example, in providing access to the user profile for the user 104 to the medical provider 110, upon a request by the medical provider 110 for such access, the profile application 120 is configured to accept an identity of the medical provider 110 (e.g., as provided by the medical provider 110 to the profile application 120 via network 118, as provided to the profile application 120 by the user 104, etc.), a designation of one or more content blocks to which access is desired, and a specified duration of such access (e.g., upon approval of or confirmation by the user 104, etc.). The profile application 120 is configured to then communicate an access command to the access engine 122 (e.g., via network 118, etc.). In turn, the access engine 122 is configured to impose the criteria of the access command, such that the medical provider 110, as identified in the access command, is able to access the designated content block(s) of the user profile for the user 104, for the duration specified. The access engine 122 is configured to then notify the medical provider 110 of the access, and eventually end the access as defined by the duration specified. Further, in addition to controlling the designated content and duration of the access, the access engine 122 is configured to permit the access as read only by the medical provider 110, or to permit the medical provider 110 to edit and/or copy content to/from the accessed content block(s), at the profile data structure 124.

The access to the user profile, when provided to a provider (as read and/or write access), may be facilitated directly between the access engine 122 and the provider. Additionally, or alternatively, the access may be provided through the communication device 116. Specifically, for example, in connection with the above example transaction between the user 104 and the merchant 102, the merchant 102 may interact with the access engine 122 (and the profile data structure 124) through the user's communication device 116, via a Bluetooth channel or a near field communication (NFC) channel, thereby relying on the physical proximity of the communication device 116 to the merchant 102 for the access. In so doing, the merchant 102 may be provided access, by the user 104, to content blocks in the user's profile relating to contact information for the user 104, payment account information for the user 104, and purchase history for the user 104. Then, upon completion of the transaction (based on the user's payment account information accessed in the user's profile), the merchant 102 may add the purchase (and information relating thereto) to the content block relating to the user's purchase history. As can be appreciated, such proximity based access at the merchant 102, in this example, may provide a level of security to the access (whereby such access is only potentially available when the user 104 is at the merchant 102).

Figure 2:
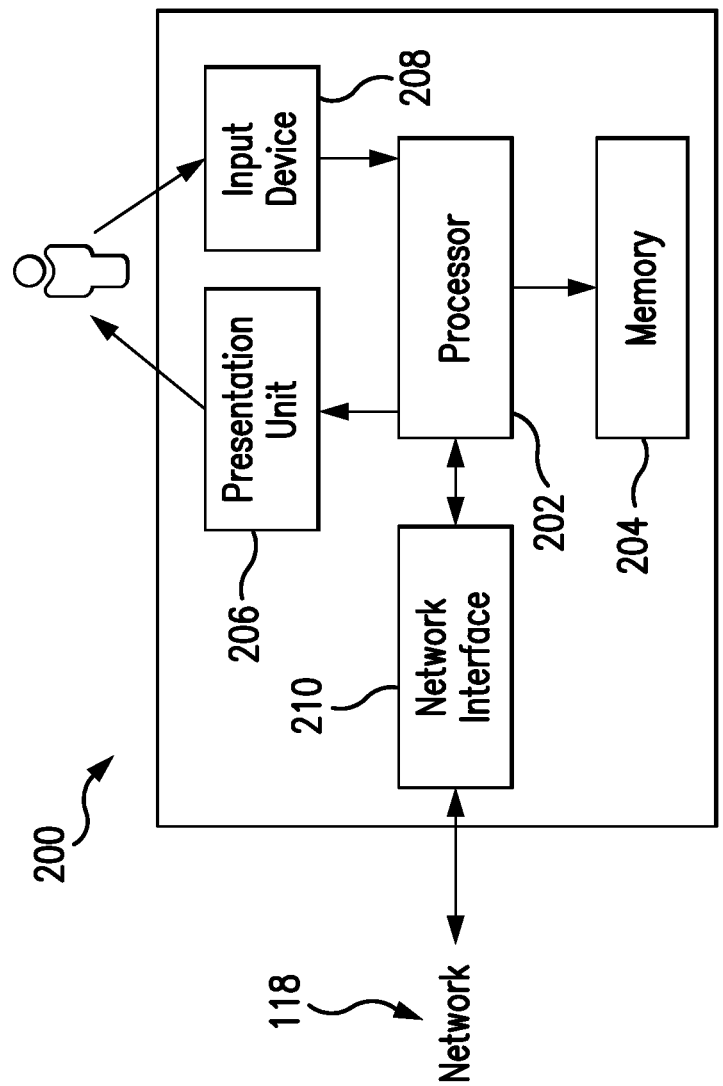
FIG. 2 is a block diagram of a computing device that may be used in the exemplary system of FIG. 1.

FIG. 2 illustrates an exemplary computing device 200 that can be used in the system 100. The computing device 200 may include, for example, one or more servers, workstations, personal computers, laptops, tablets, smartphones, POS terminals, PDAs, etc. In addition, the computing device 200 may include a single computing device, or it may include multiple computing devices located in close proximity or distributed over a geographic region, so long as the computing devices are configured to function as described herein. In the system 100, shown in FIG. 1, the merchant 102, the payment network 106, the issuer 108, and the medical provider 110, the pharmacy 112, and the education provider 114 are illustrated as including, or being implemented in, computing device 200, coupled to the network 118. In addition, the communication device 116 associated with the user 104 as well as the access engine 122 may be considered (and/or implemented in) a computing device consistent with computing device 200. However, the system 100 should not be considered to be limited to the computing device 200, as described below, as different computing devices and/or arrangements of computing devices may be used. In addition, different components and/or arrangements of components may be used in other computing devices.

Referring to FIG. 2, the exemplary computing device 200 includes a processor 202 and a memory 204 coupled to (and in communication with) the processor 202. The processor 202 may include one or more processing units (e.g., in a multi-core configuration, etc.). For example, the processor 202 may include, without limitation, a central processing unit (CPU), a microcontroller, a reduced instruction set computer (RISC) processor, an application specific integrated circuit (ASIC), a programmable logic device (PLD), a gate array, and/or any other circuit or processor capable of the operations described herein.

The memory 204, as described herein, is one or more devices that permit data, instructions, etc., to be stored therein and retrieved therefrom. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, floppy disks, tapes, hard disks, and/or any other type of volatile or nonvolatile physical or tangible computer-readable media. The memory 204 may be configured to store, without limitation, data structures, user profiles (and content blocks included therein), access commands, biometrics, interfaces, and/or other types of data (and/or data structures) suitable for use as described herein. Furthermore, in various embodiments, computer-executable instructions may be stored in the memory 204 for execution by the processor 202 to cause the processor 202 to perform one or more of the functions described herein, such that the memory 204 is a physical, tangible, and non-transitory computer readable storage media. Such instructions often improve the efficiencies and/or performance of the processor 202 that is performing one or more of the various operations herein.

In the exemplary embodiment, the computing device 200 also includes a presentation unit 206 that is coupled to (and is in communication with) the processor 202 (however, it should be appreciated that the computing device 200 could include output devices other than the presentation unit 206, etc.). The presentation unit 206 outputs information (e.g., user profile content, etc.), visually, for example, to a user of the computing device 200 such as, for example, the user 104 and/or users associated with one or more of the merchant 102, the issuer 108, the medical provider 110, the pharmacy 112, the education provider 114, etc. Various interfaces (e.g., as defined by network-based applications, websites, etc.) may be displayed at computing device 200, and in particular at presentation unit 206, to display and/or solicit certain information, as described herein. The presentation unit 206 may include, without limitation, a liquid crystal display (LCD), a light-emitting diode (LED) display, an organic LED (OLED) display, an "electronic ink" display, speakers, etc. In some embodiments, presentation unit 206 includes multiple devices.

In addition, the computing device 200 includes an input device 208 that receives inputs from the user (i.e., user inputs) such as, for example, contact information, social security number, medical information, other personal and/or account details, etc. The input device 208 is coupled to (and is in communication with) the processor 202 and may include, for example, one or more of a keyboard, a pointing device, a mouse, a stylus, a card reader, a camera, a touch sensitive panel (e.g., a touch pad or a touch screen, etc.), a biometric input device (for reading biometric data such as fingerprints, eye scans, etc.), and/or other suitable input device. Further, in various exemplary embodiments, a touch screen may behave as both a presentation unit 206 and an input device 208.

Figure 3:
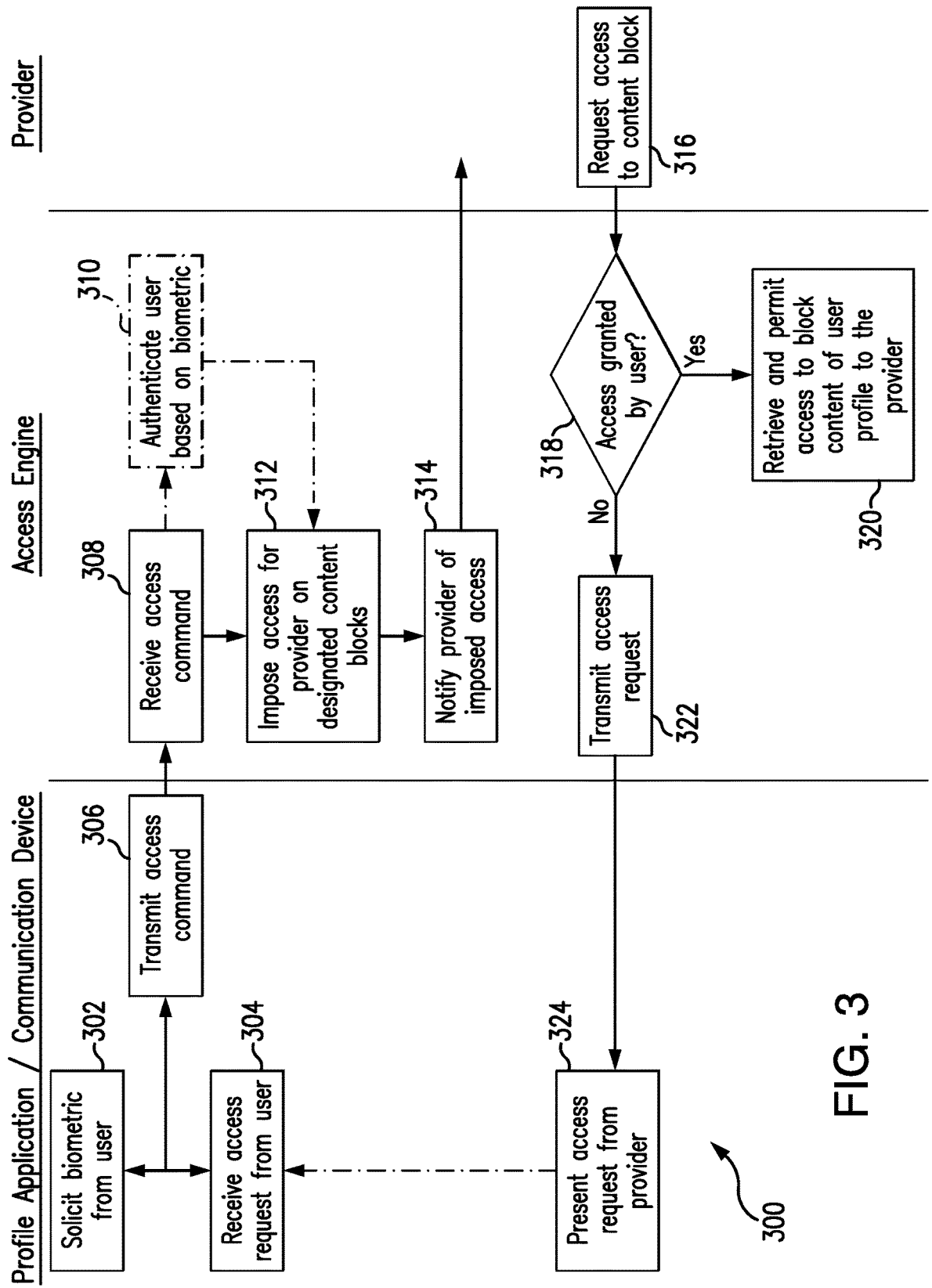
FIG. 3 is an exemplary method, which may be implemented in connection with the system of FIG. 1, for managing access, by a provider, to a user profile associated with a user in connection with the user interacting with the provider.

Further, the illustrated computing device 200 also includes a network interface 210 coupled to (and in communication with) the processor 202 and the memory 204. The network interface 210 may include, without limitation, a wired network adapter, a wireless network adapter (e.g., an NFC adapter, a Bluetooth adapter, etc.), a mobile network adapter, or other device capable of communicating to one or more different networks, including the network 118. Further, in some exemplary embodiments, the computing device 200 includes the processor 202 and one or more network interfaces incorporated into or with the processor 202. FIG. 3 illustrates an exemplary method 300 for use in managing access to a user profile for a user, and specifically, to content blocks of information within the user profile. In this exemplary embodiment, the method 300 is described with reference to the system 100 and the computing device 200. It should be appreciated, however, that the methods herein are not limited to the system 100 or to the computing device 200 as they may be implemented in other systems and/or computing devices, and that, conversely, the systems and computing devices herein are not limited to method 300.

The method 300 is described herein with reference to two separate exemplary access scenarios: one involving the medical provider 110 and the pharmacy 112, and another involving the education provider 114. It should be appreciated, however, that the method 300 is applicable to other access scenarios involving the medical provider 110, the pharmacy 112, and the education provider 114 within the scope of the present disclosure. In addition, it should also be appreciated that the method 300 is applicable to access scenarios involving other providers (e.g., the merchant 102, the issuer 108, other providers not shown in FIG. 1, etc.) within the scope of the present disclosure.

In particular, in the first access scenario, the user 104 is scheduled for a doctor's appointment with the medical provider 110. In advance of his/her appointment, the user 104 interacts with the profile application 120 (via the user's communication device 116) to provide/allow access to/by the medical provider 110 to the user's profile (as stored in the profile data structure 124). In connection therewith, the profile application 120 initially solicits, at 302, a biometric from the user 104 to authenticate the user to the profile application 120 (in order to allow the user 104 to utilize the profile application 120). The biometric may include, without limitation, a fingerprint, a facial image, or other suitable biometric, which may be captured via the communication device 116 (e.g., at the input device 208, etc.). The biometric received at the communication device 116 from the user 104 may then be compared, by the communication device 116, to reference biometric data for the user 104 previously stored at the communication device 116 (e.g., in memory 204, etc.) to authenticate the user 104 to the profile application 120, or not (e.g., based on suitable algorithms for such comparison, etc.). Alternatively, the biometric received at the communication device 116 may be included in an access command to the access engine 122, as described directly below (as biometric data), where the access engine 122 then performs the biometric comparison between the captured biometric and reference biometric data for the user 104, for example, stored at the user profile for the user 104 in the profile data structure 124.

Prior to such authentication, or subsequently therewith (depending on where the authentication is performed), the profile application 120 also receives a request from the user 104, at 304, to provide the access to the user profile for the medical provider 110. In particular, in this example, the user 104 interacts with an interface or multiple interfaces provided by the profile application 120 (as part of facilitating the request) to identify the medical provider 110 (e.g., by typing a name of the medical provider 110, by selecting the medical provider 110 from a predefined list, etc.) and to designate the appropriate content block(s) of the user profile for the access. In addition, for each designated content block, the user 104 may select a duration of such access via the profile application 120 (e.g., through the interface(s), etc.).

Because the medical provider 110 is configured to provide medical services to the user 104, as part of the request the user 104 may designate the content blocks relating to the user's contact information, medical history, allergies, and current medications for access. In so doing, the user 104 may permit indefinite access to the content block relating to the user's contact information, but may limit access to his/her medical history, allergies, and current medications for the duration/time of the user's appointment at the medical provider 110 and for a time period of twenty-four hours in advance of and after his/her appointment. Such access may include read only access for the medical provider 110 for the content block relating to the user's contact information (indefinitely), and read/write access for the content blocks relating to medical history, allergies, and current medications so that the medical provider 110 can provide updates, for example, based on the results of the user's doctor's appointment (for the duration/time of the user's appointment at the medical provider 110 and for the time period of twenty-four hours in advance of and after his/her appointment).

Subsequently, the profile application 120 compiles the access command regarding the access request and transmits the access command, via the network 118, to the access engine 122, at 306. In turn, the access engine 122 receives the access command, at 308.

Next, the access engine 122 authenticates the user 104, at 310, based on the biometric data received from the user 104 (at 302) and included in the access command, when such authentication is not performed at the communication device 116 (hence the dotted lines in FIG. 3). In particular, for example, authentication of the user 104 by the access engine 122 may include the access engine 122 retrieving reference biometric data for the user 104 from the user profile (as included in the data structure 124), and comparing the received biometric data with the reference biometric data (e.g., based on suitable algorithms for such comparison, etc.). If authentication is not successful (i.e., if the biometric data does not match), the access command is declined by the access engine 122. However, if the authentication is successful (i.e., if the biometric data matches), the access engine 122 proceeds to impose access for the medical provider 110, at 312, on the designated content blocks from the user's initial request. Alternatively, when authentication of the user 104 is performed at the communication device 116, the access engine 122, upon receiving the access command from the profile application 120 (at 308), simply imposes access for the medical provider 110 (at 312) consistent with the access command. Then, in either case, after imposing the appropriate access to the medical provider 110 (at 312), the access engine 122 transmits a notification to the medical provider 110, at 314, indicating the granted access. This may include transmitting the notification to the medical provider 110 via email or otherwise, as desired.

With continued reference to FIG. 3, in advance of the doctor's appointment for the user 104 in this first scenario, the medical provider 110 may request access to the user profile for the user 104, at 316, and specifically, to particular ones of the content blocks included therein as required or desired in advance of the doctor's appointment (e.g., the content blocks relating to the user's contact information, medical history, allergies, and current medications; etc.). This may be done upon receipt of the notification from the access engine 122 (as transmitted at 314), for example, when the user 104 is not physically present at the medical provider 110 to grant such access. Or, this may be done by the medical provider 110 at its own initiative (e.g., prior to the user 104 granting such access, such that the method 300 may actually start with the request by the medical provider 110, at 316; etc.).

In this example, the medical provider 110 directs the access request to the access engine 122. As such, in response, the access engine 122 determines, at 318, whether access has already been granted to the medical provider 110 for the user profile and the particular content blocks identified by the medical provider 110, at the time of the medical provider's request. In so doing, the access engine 122 may initially determine if the access request received from the medical provider 110 is within the duration for which the user 104 has granted such access. The access engine 122 may then determine if the content blocks of the user's profile identified in the access request from the medical provider 110 correspond to the content blocks for which the user 104 has allowed access. When the access engine 122 determines that access has been granted by the user 104 to the medical provider 110, the access engine 122 retrieves/identifies the appropriate information from the user profile for the content blocks identified in the access request by the medical provider 110, at 320, and permits access thereto in the profile data structure 124 by the medical provider 110. This may include modifying a permission associated with the user profile, in the profile data structure 124, to designate the particular content blocks as accessible therein by the medical provider 110.

However, when the access engine 122 determines, at 318, that access has not yet been granted, the access engine 122 transmits an access request to the profile application 120, at 322. This access request generally includes access for any content blocks that may not have been included in the user's original access command. In turn, the profile application 120 presents the new access request to the user 104, at 324. And, if the user 104 grants the requested access, the profile application 120 may (as indicated by the dotted lines in FIG. 3) process the request in the same manner described above (at 304) for the access request received from the user 104. Alternatively, when the profile application 120 receives the access request from the provider (at 324), and the user 104 grants the request, the requested content block(s) may simply be returned by the access engine 122 directly to the medical provider 110 (without further processing the request at 304).

As indicated above, in this first scenario, the access command originally received from the profile application 120 (at 308) included a duration for which the medical provider 110 is permitted to access the user profile (i.e., for the duration/time of the user's appointment at the medical provider 110 and for a time period of twenty-four hours in advance of his/her appointment). The access command also designated access to the user profile for the content blocks relating to the user's contact information, medical history, allergies, and current medications. As such, if the access request by the medical provider 110 is made two hours prior to the user's appointment, for example, it is within the duration specified by the user 104. And, as indicated above, because the access request by the medical provider 110 included/designated the same content blocks as identified by the user 104 (i.e., the content blocks relating to the user's contact information, medical history, allergies, and current medications), the access engine 122 will proceed to retrieve and/or permit access to the content blocks (at 320) of the user's profile in the profile data structure 124, as requested for access by the medical provider 110 and as designated by the user 104.

Conversely, if the access request by the medical provider 110 further includes/designates a content block from the user profile relating to payment account information and/or insurance information (which is not included in the original access command received from the profile application 120), the access engine 122 then transmits an additional prompt to the profile application 120 for the appropriate content block(s) (at 322). In turn, the profile application 120 solicits permission for such additional access from the user 104 (at 324). And when granted, whether authentication of the user 104 is required again or not, the profile application 120 compiles and transmits another access command to the access engine 122 (at 306), and the access engine 122 responds in the manner described above (at 308-314), thereby imposing the additional access to the medical provider 110 as appropriate. Or, as indicated above, the access engine 122 may simply return the requested content block(s) directly to the medical provider 110 (without further processing the request (at 308-314).

Continuing with this first access scenario, during the doctor's appointment, the physician may recommend a particular medication for the user 104, requiring a prescription. In so doing, the medical provider 110 edits a content block of the user profile to include the prescription (e.g., adds the prescription to a current content block to which the medical provider 110 has access, requests access to another prescription content block (at 322), creates a new prescription content block, etc.).

In response, the user 104 interacts with the profile application 120 (via the user's communication device 116) to provide/allow access to/by the pharmacy 112 to the user's profile (as stored in the profile data structure 124). In particular, the profile application 120 initially solicits, at 302, a biometric from the user 104 to authenticate the user to the profile application 120, as described above (if such authentication is necessary). The profile application also receives a request from the user 104, at 304, for the access to the user profile for the pharmacy 112. Here, as part of the request, the user 104 may designate the content blocks relating to the user's contact information, allergies, and current medications for access to the pharmacy 112. In so doing, the user 104 may permit indefinite access to the content block relating to the user's contact information, but may limit access to his/her allergies and current medications for a time period of twenty-four hours following such request (in order to allow the pharmacy 112 time to process the required prescription).

In turn, the profile application 120 compiles the access command regarding the access request and transmits the access command, via the network 118, to the access engine 122, at 306. And, the access engine 122 receives the access command, at 308. Next, as necessary (i.e., if the user 104 is not already authenticated at the communication device 116), the access engine 122 authenticates the user 104, at 310, based on the biometric data received from the user 104 (at 302) and included in the access command. When the user 104 is authenticated (be it at the communication device 116 or at the access engine 122), the access engine 122 proceeds to impose access for the pharmacy, at 312, on the designated content blocks from the user's initial request (i.e., from the access command). Then, the access engine 122 transmits a notification to the pharmacy 112, at 314, indicating the granted access. Alternatively, in a synchronous scenario, the access engine 122 may simply transmit the requested data to the pharmacy 112, for example, as part of (or as a continuation of) the original access request regarding the medical provider 110.

Subsequently, in advance of processing the prescription for the user 104 (e.g., upon receipt of the notification from the access engine 122, as transmitted at 314; etc.), the pharmacy 112 requests access to the user profile for the user 104, at 316, and specifically, to particular ones of the content blocks included therein as required or desired in order to process the prescription (if such access is not already granted). For example, the pharmacy 112 may request access to the content blocks relating to the user's contact information, allergies, current medications, and insurance information.

The pharmacy 112 again directs the access request to the access engine 122. In response, the access engine 122 determines, at 318, whether access has been granted to the pharmacy 112 for the user profile and the particular content blocks identified by the pharmacy 112. In so doing, the access engine 122 may initially determine if the access request received from the pharmacy 112 is within the duration for which the user 104 granted access. The access engine 122 may then determine if the content blocks of the user profile identified in the access request from the pharmacy 112 correspond to the content blocks for which the user 104 has allowed access. Here, the access command received from the profile application 120 (at 308) included a duration of access for the pharmacy 112 of twenty-four hours. The access command also designated access to the user profile for the content blocks relating to the user's contact information, allergies, and current medications. As such, if the access request by the pharmacy 112 is made two hours after receiving the prescription, for example, it is within the duration specified by the user 104. However, because the access request by the pharmacy 112 included/designated an additional content block related to insurance information for the user 104, the access engine 122 denies access to this content block and transmits another access request to the profile application 120, at 322, for the insurance content block. In turn, the profile application 120 solicits permission for such additional access from the user 104. And when granted, whether authentication of the user 104 is required again or not, the access engine 122 compiles and transmits an access command to the access engine 122 (at 306), which responds in the manner described above (at 308-314), thereby imposing the additional access to the pharmacy 112. And, the access engine 122 then proceeds to retrieve and permit access to the content blocks (at 320) in the profile data structure 124, as requested for access by the pharmacy 112 and as designated by the user 104. Or, as indicated above, the access engine 122 may simply return the requested content block(s) directly to the pharmacy 112 (without further processing the request (at 308-314).

In the above access scenario, the access requests from the medical provider 110 and the pharmacy 112 are received by the access engine 122. It should be appreciated, however, that the access requests may instead be received by the profile application 120 (at the user's communication device 116) in other implementations (whereby the medical provider 110 and/or the pharmacy 112 then interact with the access engine 122 via the profile application 120, etc.). For example, the pharmacy 112 may interact with the user's communication device 116 (and the profile application 120) via an NFC channel, thereby relying on the physical proximity of the communication device 116 to the pharmacy 112 for the access. In so doing, the pharmacy 112 may be provided access, by the user 104, to the content blocks in the user's profile relating to the prescription from the medical provider 110, allergies, and insurance information. In this manner, the pharmacy 112 can then process the prescription for the user 104, while the user is present at the pharmacy 112.

In the second access scenario, a child of the user 104 needs a permission authorization from the user 104 in order for the education provider 114 to permit the child to attend a field trip.

In this access scenario, at the beginning of the child's school year, the user 104 may interact with the profile application 120 (via the user's communication device 116) to provide/allow access to/by the education provider 114 to the user's profile (as stored in the profile data structure 124). In particular, the profile application 120 initially solicits, at 302, a biometric from the user 104 to authenticate the user to the profile application 120, as described above (if such authentication is necessary). The profile application 120 also receives a request from the user 104, at 304, for the access to the user profile for the education provider 114. Here, as part of the request, the user 104 may designate content blocks relating to the user's contact information and relating to permission authorization for the user's child. In so doing, the user 104 may permit access to the content blocks by the education provider 114 for the duration of the school year, and may also permit both read and write access to the content block relating to the permission forms so that the education provider 114 can add permission forms as necessary.

In turn, the profile application 120 compiles the access command regarding the access request and transmits the access command, via the network 118, to the access engine 122, at 306. The access engine 122 receives the access command, at 308. In response, as necessary (i.e., if the user 104 is not already authenticated at the communication device 116), the access engine 122 authenticates the user 104, at 310, based on the biometric data received from the user 104 (at 302) and included in the access command. And, when the user 104 is authenticated (be it at the communication device 116 or at the access engine 122), the access engine 122 proceeds to impose access for the education provider 114, at 312, on the designated content blocks from the user's initial request (i.e., from the access command). Then, the access engine 122 transmits a notification to the education provider 114, at 314, indicating the granted access.

Next in this access scenario, in advance of the child's field trip, the education provider 114 requests access to the user profile for the user 104, at 316, and specifically, to the content block relating to permission authorization for the user's child. The education provider 114 directs the access request to the access engine 122 and, in response, the access engine 122 determines, at 318, whether access has been granted to the education provider 114 for the user profile and the particular content block relating to permission authorization for the user's child. In so doing, the access engine 122 may initially determine if the access request received from the education provider 114 is within the duration for which the user 104 granted access. The access engine 122 may then determine if the content block identified in the access request from the education provider 114 corresponds to one of the content blocks for which the user 104 has allowed access. Here, because the access request by the education provider 114 is received during the school year and includes/designates a content block also identified by the user 104 in the access command, the access engine 122 will proceed to retrieve and/or permit access to the content block (at 320) in the profile data structure 124, as requested by the education provider 114. In so doing, the education provider 114 is permitted to add the required permission authorization to the content block, in the profile data structure 124, relating to the requested permission for the user's child.

Then, once the permission authorization is added to the user profile by the education provider 114, the user 104 is able to access it and sign it as needed (and store the signed copy in the user profile, in the content block relating to the permission authorization). And, again through the access to the content block relating to the permission forms already provided to the education provider 114, as described above, the education provider 114 can again access the content block and retrieve the signed permission authorization.

In view of the above, the systems and methods herein may enable users to generate standardized profiles, and exchange information contained in the profiles with desired recipients (e.g., providers, etc.), for example, based on granting of permissions by the users to the recipients associated with the desired information exchange. In particular, users are able to compile profiles that contain multiple content blocks of different information related to the users, and to grant access to the profiles (and/or the content blocks therein) to select recipients so that the recipients can either retrieve desired or required information about the users (and/or other people associated with the users) from the profiles or add information to the profiles. Thus, through the systems and methods herein, the users are provided with repositories of information in their profiles, which may be "opened" at the discretion (and permission) of the users for select recipients to access, without a need to separately and repeatedly provide the same information to different recipients.

Again and as previously described, it should be appreciated that the functions described herein, in some embodiments, may be described in computer executable instructions stored on a computer readable media, and executable by one or more processors. The computer readable media is a non-transitory computer readable storage medium. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Combinations of the above should also be included within the scope of computer-readable media.

It should also be appreciated that one or more aspects of the present disclosure transforms a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques including computer software, firmware, hardware or any combination or subset thereof, wherein the technical effect may be achieved by performing at least one of: (a) receiving a request from a recipient to access at least one content block in a user profile associated with a user; (b) verifying that access is granted by the user to the at least one content block included in the request from the recipient; (c) when access is granted by the user to the at least one content block, exposing the at least one content block to the recipient consistent with the granted access; (d) when access is not granted by the user to the at least one content block, transmit a notification to the user, at a communication device associated with the user, requesting grant of access to the at least one content block for the recipient; (e) receiving, from the user via the communication device, an access command regarding grant of access to the at least one content block, the access command including a designation of the at least one content block and a duration of the granted access to the at least one content block; (f) terminating the granted access to the at least one content block when the duration of the access expires; and (g) notifying the recipient of the granted access, when the at least one of the multiple content blocks is exposed to the recipient.

Exemplary embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular exemplary embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "included with," or "in communication with" another feature, it may be directly on, engaged, connected, coupled, associated, included, or in communication to or with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

The foregoing description of exemplary embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for use in implementing access controls to content blocks of a user profile associated with a user, the system comprising:

a memory including a user profile for a user, the user profile including multiple content blocks, each of the content blocks of the user profile associated with a permission and including content related to the user, wherein the multiple content blocks include a first content block having one or more of a payment account credential associated with the user, insurance information associated with the user, and medical information associated with the user; and an access engine computing device coupled to the memory and configured to:

receive an access command from the user via a communication device, the access command including a designation of the first content block for access by a provider and an identity of the provider;

modify the permission associated with the first content block in relation to the provider to permit the access by the provider, wherein the access includes read access and/or write access for the first content block;

in response to the communication device being in proximity to the provider and based on the modified permission, expose the first content block to the provider, thereby granting the access for the provider to the first content block; and in response to the communication device being out of proximity to the provider and based on the modified permission, terminate the access of the provider to the first content block, thereby defining a duration of the access to the first content block by the proximity of the communication device to the provider.

2. The system of claim 1, wherein the access engine computing device is further configured to receive a request, from the provider, to access at least one of the multiple content blocks; and
   wherein the access engine computing device is configured, in connection with exposing the first content block to the provider, to expose the first content block to the provider in response to the at least one of the multiple content blocks matching the first content block.

3. The system of claim 2, wherein the access engine computing device is further configured to solicit the user via the communication device to grant the access to the provider for the at least one of the multiple content blocks included in the request received from the provider, in response to said at least one of the multiple content blocks being different from the first content block.

4. The system of claim 1, wherein the access engine computing device is further configured to:
   in response to expiration of the duration of the access, terminate the access of the provider to the first content block.

5. The system of claim 1, wherein the access engine computing device is further configured to notify the provider of the access, in response to the first content block being exposed to the provider.

6. The system of claim 1, wherein the access consists of a read-only access.

7. The system of claim 1, wherein the access engine computing device is configured, in connection with exposing the first content block to the provider, to transmit the first content block to the provider; and
   wherein the first content block, when transmitted, includes a header indicating a content block type of the first content block.

8. The system of claim 1, wherein the multiple content blocks included in the user profile for the user are each formatted according to a same standard format.

9. The system of claim 1, wherein the access engine computing device is further configured to authenticate the user, prior to exposing the first content block to the provider.

10. A computer-implemented method for granting access to content blocks in a user profile associated with a user, the method comprising:
    receiving, by a computing device, a request from a recipient to access at least one content block in a user profile associated with a user, wherein the access includes read access and/or write access for the at least one content block;
    verifying, by the computing device, that access to the at least one content block is granted by the user;
    in response to access being granted by the user to the at least one content block, exposing, by the computing device, the at least one content block to the recipient consistent with the access only when a communication device associated with the user is at a location of the recipient, thereby defining a duration of the access by the communication device being at the location of the recipient; and
    in response to access not being granted by the user to the at least one content block, transmitting a notification to the user, at the communication device associated with the user, including a request for grant of access to the at least one content block for the recipient.

11. The computer-implemented method of claim 10, further comprising receiving, by the computing device, from the user via the communication device, an access command regarding grant of access to the at least one content block, the access command including a designation of the at least one content block and a designation of the recipient.

12. The computer-implemented method of claim 11, further comprising terminating the access to the at least one content block when the communication device associated with the user is not at the location of the recipient.

13. The computer-implemented method of claim 11, wherein the access command regarding the grant of access to the at least one content block in the user profile associated with the user is received by the computing device prior to the request from the recipient to access the at least one content block.

14. The computer-implemented method of claim 11, wherein the access command regarding the at least one content block is received by the computing device in response to an access request from the computing device, based on the request from the recipient.

15. The computer-implemented method of claim 10, further comprising notifying, by the computing device, the recipient of the granted access, when the at least one content block is exposed to the recipient.

16. A non-transitory computer-readable storage medium including executable instructions for granting access to content blocks in a user profile associated with a user, which when executed by at least one processor, cause the at least one processor to:
    receive a request from a recipient to access at least one content block in a user profile associated with a user, wherein the access includes read access and/or write access for the at least one content block;
    verify that access to the at least one content block is granted by the user;
    in response to access being granted by the user to the at least one content block, expose the at least one content block to the recipient consistent with the access only when a communication device associated with the user is at a location of the recipient, thereby defining a duration of the access by the communication device being at the location of the recipient; and
    in response to access not being granted by the user to the at least one content block, transmit a notification to the user, at the communication device associated with the user, including a request for grant of access to the at least one content block for the recipient.

17. The non-transitory computer-readable storage medium of claim 16, wherein the executable instructions, when executed by the at least one processor, further cause the at least one processor to receive, from the user via the communication device, an access command regarding grant of access to the at least one content block, the access command including a designation of the at least one content block and a designation of the recipient; and
    wherein the executable instructions, when executed by the at least one processor, cause the at least one processor, in connection with verifying that access to the at least one content block is granted by the user, to verify that the access to the at least one content block is granted by the user based on the access command.

18. The non-transitory computer-readable storage medium of claim 16, wherein the executable instructions, when executed by the at least one processor, further cause the at least one processor to terminate the granted access to the at least one content block when the communication device associated with the user is not at the location of the recipient.

19. The non-transitory computer-readable storage medium of claim 16, wherein the executable instructions, when executed by the at least one processor, further cause the at least one processor to notify the recipient of the granted access, when the at least one content block is exposed to the recipient.

* * * * *